(12) United States Patent
Mylari

(10) Patent No.: US 6,380,200 B1
(45) Date of Patent: Apr. 30, 2002

(54) COMBINATION OF ALDOSE REDUCTASE INHIBITORS AND SELECTIVE SEROTONIN REUPTAKE INHIBITORS FOR THE TREATMENT OF DIABETIC COMPLICATIONS

(75) Inventor: Banavara L. Mylari, Waterford, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/727,964

(22) Filed: Dec. 1, 2000

Related U.S. Application Data

(60) Provisional application No. 60/169,462, filed on Dec. 7, 1999.

(51) Int. Cl.$^7$ .................... A61K 31/495; A61K 31/535; A61K 31/445; A61K 31/425; A61K 31/40
(52) U.S. Cl. ........................ 514/252.14; 514/231.2; 514/231.5; 514/315; 514/365; 514/366; 514/367; 514/391; 514/409; 514/415; 514/450; 514/646; 514/647; 514/866
(58) Field of Search .......................... 514/252.14, 365, 514/366, 367, 866, 391, 450, 315, 647, 646, 409, 415, 231.2, 231.5, 555

(56) References Cited

U.S. PATENT DOCUMENTS

| | | | |
|---|---|---|---|
| 3,912,743 A | 10/1975 | Christensen et al. ... | 260/293.58 |
| 4,536,518 A | 8/1985 | Welch, Jr. et al. .......... | 514/647 |
| 4,734,419 A | 3/1988 | Hashimoto et al. ......... | 514/259 |
| 4,883,800 A | 11/1989 | Hashimoto et al. ......... | 514/259 |
| 4,929,629 A | 5/1990 | Jeffery ........................ | 514/646 |
| 4,939,140 A | 7/1990 | Larson et al. ................ | 514/222 |
| 5,866,578 A * | 2/1999 | Mylari et al. ................ | 514/256 |
| 5,990,111 A * | 11/1999 | Johnson ....................... | 514/252 |
| 6,294,538 B1 * | 9/2001 | Mylari .................. | 514/252.14 |

* cited by examiner

*Primary Examiner*—Kevin E. Weddington
(74) *Attorney, Agent, or Firm*—Peter C. Richardson; Gregg C. Benson; Robert T. Barker

(57) ABSTRACT

This invention is directed to methods, pharmaceutical compositions and kits comprising an aldose reductase inhibitor (ARI), a prodrug thereof or a pharmaceutically acceptable salt of said ARI or said prodrug and selective serotonin reuptake inhibitor (SSRI), a prodrug thereof or a pharmaceutically acceptable salt of said SSRI or said prodrug. This invention further relates to methods of using those pharmaceutical compositions for the treatment of diabetic complications such as diabetic neuropathy, diabetic nephropathy, diabetic retinopathy, myocardial infarction, cataracts and diabetic cardiomyopathy.

27 Claims, No Drawings

COMBINATION OF ALDOSE REDUCTASE INHIBITORS AND SELECTIVE SEROTONIN REUPTAKE INHIBITORS FOR THE TREATMENT OF DIABETIC COMPLICATIONS

This application is filed claiming priority from co-pending Provisional Application No. 60/169,462 filed Dec. 7, 1999.

BACKGROUND OF THE INVENTION

This invention relates to methods, pharmaceutical compositions and kits comprising an aldose reductase inhibitor (ARI), a prodrug thereof or a pharmaceutically acceptable salt of said ARI or said prodrug and a selective serotonin reuptake inhibitor (SSRI), a prodrug thereof or a pharmaceutically acceptable salt of said SSRI or said prodrug. This invention further relates to methods of using such pharmaceutical compositions for the treatment of diabetic complications such as diabetic neuropathy, diabetic nephropathy, diabetic retinopathy, myocardial infarction, cataracts and diabetic cardiomyopathy.

Aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way, unwanted accumulations of galactitol in the lens of galactosemic subjects and of sorbitol in the lens, peripheral nervous cord and kidneys of various diabetic subjects are prevented or reduced. Accordingly, aldose reductase inhibitors are of therapeutic value for controlling certain diabetic complications, e.g., diabetic neuropathy, diabetic nephropathy, diabetic cardiomyopathy, myocardial infarction, cataracts and diabetic retinopathy.

Selective serotonin reuptake inhibitors function by inhibiting the reuptake of serotonin by afferent neurons.

SUMMARY OF THE INVENTION

This invention is directed to pharmaceutical compositions comprising an aldose reductase inhibitor (ARI), a prodrug thereof or a pharmaceutically acceptable salt of said ARI or of said prodrug; a selective serotonin reuptake inhibitor (SSRI), a prodrug thereof or a pharmaceutically acceptable salt of said SSRI or of said prodrug; and a pharmaceutically acceptable carrier, vehicle or diluent.

This invention is also directed to methods of treating a diabetic complication in a mammal comprising administering to said mammal a pharmaceutical composition as set forth hereinbelow. In particular, such diabetic complications as, for example, diabetic neuropathy, diabetic nephropathy, diabetic cardiomyopathy, myocardial infarction, cataracts and diabetic retinopathy can be treated by the methods of this invention.

This invention is also directed to methods of treating a diabetic complication in a mammal comprising administering to said mammal an ARI, a prodrug thereof or a pharmaceutically acceptable salt of said ARI or said prodrug; and an SSRI, a prodrug thereof or a pharmaceutically acceptable salt of said SSRI or said prodrug.

This invention is especially directed to methods wherein the ARI, prodrug thereof or pharmaceutically acceptable salt of said ARI or said prodrug, and the SSRI, prodrug thereof or pharmaceutically acceptable salt of said SSRI, are administered separately.

This invention is also especially directed to methods wherein the ARI, prodrug thereof or pharmaceutically acceptable salt of said ARI or said prodrug, and the SSRI, prodrug thereof or pharmaceutically acceptable salt of said SSRI or said prodrug are administered together.

This invention is also directed to kits comprising:

a) a first unit dosage form comprising an aldose reductase inhibitor (ARI), a prodrug thereof or a pharmaceutically acceptable salt of said ARI or said prodrug and a pharmaceutically acceptable carrier, vehicle or diluent;

b) a second unit dosage form comprising a selective serotonin reuptake inhibitor (SSRI), a prodrug thereof or a pharmaceutically acceptable salt of said SSRI or said prodrug and a pharmaceutically acceptable carrier, vehicle or diluent; and c) a container.

In the compositions, methods and kits of this invention, it is preferred that said ARI is fidarestat, epalrestat, minalrestat, SPR-210, zenarestat or zopolrestat, a prodrug thereof or a pharmaceutically acceptable salt of said ARI or of said prodrug. It is especially preferred that said ARI is zopolrestat, a prodrug thereof or a pharmaceutically acceptable salt thereof or of said prodrug.

In the compositions, methods and kits of this invention, it is preferred that said selective serotonin reuptake inhibitor (SSRI) is femoxetine, fluoxetine, fluvoxamine, indalpine, indeloxazine, milnacipran, paroxetine, sertraline, sibutramine or zimeldine, a prodrug thereof or a pharmaceutically acceptable salt of said SSRI or of said prodrug. It is especially preferred that said SSRI is fluoxetine, sertraline or sibutramine. It is even more especially preferred that said SSRI is sertraline or fluoxetine.

DETAILED DESCRIPTION OF THE INVENTION

The methods, compositions and kits of this invention are useful in treating diabetic complications, including, but not limited to, diabetic neuropathy, diabetic nephropathy, diabetic cardiomyopathy, myocardial infarction, cataracts and diabetic retinopathy.

The term "treating", as used herein, refers to retarding, arresting or reversing the progress of, or alleviating or preventing either the disorder or condition to which the term "treating" applies, or one or more symptoms of such disorder or condition. The term "treatment", as used herein, refers to the act of treating a disorder, symptom or condition, as the term "treating" is defined above.

Any aldose reductase inhibitor may be used in the pharmaceutical compositions, methods and kits of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. No. 4,251,528; U.S. Pat. No. 4,600,724; U.S. Pat. No. 4,464,382, U.S. Pat. No. 4,791,126, U.S. Pat. No. 4,831,045; U.S. Pat. Nos. 4,734,419; 4,883,800; U.S. Pat. No. 4,883,410; U.S. Pat. No. 4,883,410; U.S. Pat. No. 4,771,050; U.S. Pat. No. 5,252,572; U.S. Pat. No. 5,270,342; U.S. Pat. No. 5,430,060; U.S. Pat. No. 4,130,714; U.S. Pat.

No. 4,540,704; U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,980,357; U.S. Pat. No. 5,066,659; U.S. Pat. No. 5,447,946; U.S. Pat. No. 5,037,831.

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound.

Accordingly, examples of aldose reductase inhibitors useful in the compositions, methods and kits of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl}-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1(2H)-quinazolineacetic acid (zenarestat, U.S. Pat. No. 4,734,419, and U.S. Pat. No. 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2', 5'-dione (U.S. Pat. No. 4,540,704);
12. 2-fluoro-spiro(9H-fluorene-9,4'-imidazolidine)-2', 5'-dione (U.S. Pat. No. 4,438,272);
13. 2,7-di-fluoro-spiro(9H-fluorene-9,4'-imidazolidine)-2', 5'-dione (U.S. Pat. No. 4,436,745, U.S. Pat. No. 4,438,272);
14. 2,7-di-fluoro-5-methoxy-spiro(9H-fluorene-9,4'-imidazolidine)-2', 5'-dione (U.S. Pat. No. 4,436,745, U.S. Pat. No. 4,438,272);
15. 7-fluoro-spiro(5H-indenol[1,2-b]pyridine-5,3'-pyrrolidine)-2,5'-dione (U.S. Pat. No. 4,436,745, U.S. Pat. No. 4,438,272);
16. d-cis-6'-chloro-2', 3'-dihydro-2'-methyl-spiro-(imidazolidine-4,4'-4'H-pyrano(2,3-b)pyridine)-2,5-dione (U.S. Pat. No. 4,980,357);
17. spiro[imidazolidine-4,5'(6H)-quinoline]-2,5-dione-3'-chloro-7,'8'-dihydro-7'-methyl-(5'-cis) (U.S. Pat. No. 5,066,659);
18. (2S,4S)-6-fluoro-2', 5'-dioxospiro(chroman-4,4'-imidazolidine)-2-carboxamide (fidarestat, U.S. Pat. No. 5,447,946); and
19. 2-[(4-bromo-2-fluorophenyl)methyl]-6-fluorospiro[isoquinoline-4(1H),3'-pyrrolidine]-1,2', 3,5'(2H)-tetrone (minalrestat, U.S. Pat. No. 5,037,831).

Other aldose reductase inhibitors include compounds of formula A,

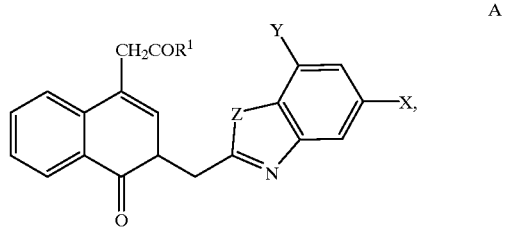

and pharmaceutically acceptable salts thereof, wherein

Z in the compound of formula A is O or S;

$R^1$ in the compound of formula A is hydroxy or a group capable of being removed in vivo to produce a compound of formula A wherein $R^1$ is OH; and X and Y in the compound of formula A are the same or different and are selected from hydrogen, trifluoromethyl, fluoro, and chloro.

A preferred subgroup within the above group of aldose reductase inhibitors includes numbered compounds 1, 2, 3, 4, 5, 6, 9,10, and 17, and the following compounds of formula A:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl) phthalazin-1 -ylacetic acid [$R^1$=hydroxy; X=$CF_3$; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1 -phthalazineacetic acid, 3,4-dihydro-4-oxo-3-[[5-(trifluoromethyl)- 2-benzothiazolyl]methyl]-[$R^1$=hydroxy; X=trifluoromethyl; Y=H].

In compounds 20–23 and 29, Z is S. In compounds 24–28, Z is O.

Of the above subgroup, compounds 20–29 are more preferred with compound 29 especially preferred.

Said compounds of formula A are prepared as disclosed in U.S. Pat. No. 4,939,140.

The aldose reductase inhibitor compounds of this invention are readily available or can be easily synthesized by those skilled in the art using conventional methods of organic synthesis, particularly in view of the pertinent patent specifications.

Any selective serotonin reuptake inhibitor (SSRI) may be used in the pharmaceutical compositions, methods and kits of this invention. The term selective serotonin reuptake inhibitor refers to a compound which inhibits the reuptake of serotonin by afferent neurons. Such inhibition is readily determined by those skilled in the art according to standard assays such as those disclosed in U.S. Pat. No. 4,536,518 and other U.S. patents recited in the next paragraph.

Preferred selective serotonin reuptake inhibitors (SSRI) which may be used in accordance with this invention include, but are not limited to: femoxetine, which may be prepared as described in U.S. Pat. No. 3,912,743; fluoxetine, which may be prepared as described in U.S. Pat. No. 4,314,081; fluvoxamine, which may be prepared as described in U.S. Pat. No. 4,085,225; indalpine, which may be prepared as described in U.S. Pat. No. 4,064,255; indeloxazine, which may be prepared as described in U.S. Pat. No. 4,109,088; milnacipran, which may be prepared as described in U.S. Pat. No. 4,478,836; paroxetine, which may be prepared as described in U.S. Pat. No. 3,912,743 or U.S. Pat. No. 4,007,196; sertraline, which may be prepared as described in U.S. Pat. No. 4,536,518; sibutramine, which may be prepared as described in U.S. Pat. No. 4,929,629; and zimeldine, which may be prepared as described in U.S. Pat. No. 3,928,369. Fluoxetine is also known as Prozac®. Sertraline is also known as Zoloft®. Sibutramine is also known as Meridia®. The disclosures thereof are incorporated herein by reference.

The expression "pharmaceutically acceptable salts" includes both pharmaceutically acceptable acid addition salts and pharmaceutically acceptable cationic salts, where appropriate. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Pharmaceutically acceptable salts of the aldose reductase inhibitors of this invention may be readily prepared by reacting the free acid form of said aldose reductase inhibitor with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), and employing a solvent (e.g., ethyl acetate) from which the desired cationic salt precipitates, or can be otherwise isolated by concentration and/or addition of a non-solvent.

The acid addition salts of the aldose reductase inhibitors of this invention may be readily prepared by reacting the free base form of said aldose reductase inhibitor with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The pharmaceutically acceptable acid addition and cationic salts of the selective serotonin reuptake inhibitors used in the combination of this invention may be prepared in a manner analogous to that described for the preparation of the pharmaceutically acceptable acid addition and cationic salts of said aldose reductase inhibitors, but substituting the desired SSRI for said aldose reductase inhibitor.

In addition, the aldose reductase inhibitors and selective serotonin reuptake inhibitors which may be used in accordance with this invention, prodrugs thereof and pharmaceutically acceptable salts thereof or of said prodrugs, may occur as hydrates or solvates. Said hydrates and solvates are also within the scope of the invention.

This invention relates both to methods of treating diabetic complications in which the ARI and selective serotonin reuptake inhibitor are administered together, as part of the same pharmaceutical composition, and to methods in which these two agents are administered separately, as part of an appropriate dosage regimen designed to obtain the benefits of the combination therapy. The appropriate dosage regimen, the amount of each dose administered and the intervals between doses of the active agents will depend upon the ARI and the selective serotonin reuptake inhibitor being used, the type of pharmaceutical formulations being used, the characteristics of the subject being treated and the severity of the complications. Generally, in carrying out the methods of this invention, an effective dosage for the aldose reductase inhibitors of this invention is in the range of about 0.01 mg/kg/day to about 100 mg/kg/day in single or divided doses, preferably 0.1 mg/kg/day to 20 mg/kg/day in single or divided doses and the selective serotonin reuptake inhibitor will be administered in single or divided doses. Selective serotonin reuptake inhibitors will generally be administered in amounts ranging from about 0.01 mg/kg/day to about 500 mg/kg/day in single or divided doses, preferably 10 mg to about 300 mg per day for an average subject, depending upon the selective serotonin reuptake inhibitor and the route of administration. However, some variation in dosage will necessarily occur depending on the condition of the subject being treated. The prescribing physician will, in any event, determine the appropriate dose for the individual subject.

Administration of the pharmaceutical compositions of this invention can be via any method which delivers a composition of this invention preferentially to the desired tissue (e.g., nerve, kidney, retina and/or cardiac tissues). These methods include oral routes, parenteral, intraduodenal routes, etc. Generally, the compositions of the present invention are administered in single (e.g., once daily) or multiple doses or via constant infusion.

Pharmaceutical compositions comprising an aldose reductase inhibitor, a prodrug thereof or a pharmaceutically acceptable salt of said aldose reductase inhibitor or said prodrug and a selective serotonin reuptake inhibitor, a prodrug thereof or a pharmaceutically acceptable salt of said selective serotonin reuptake inhibitor or said prodrug are hereinafter referred to, collectively, as "the active compositions of this invention."

The active compositions of this invention may be administered to a subject in need of treatment by a variety of conventional routes of administration, including orally, topically, parenterally, e.g., intravenously, subcutaneously or intramedullary. Further, the active compositions of this invention may be administered intranasally, as a rectal suppository or using a "flash" formulation, i.e., allowing the medication to dissolve in the mouth without the need to use water.

The active compositions of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the active compositions of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

For buccal administration the composition (two active agents administered together or separately) may take the form of tablets or lozenges formulated in a conventional manner.

For intranasal administration or administration by inhalation, the active compounds of the invention (two active agents administered together or separately) are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound or compounds of the invention and a suitable powder base such as lactose or starch.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

The active compositions of this invention contain an amount of both an aldose reductase inhibitor, a prodrug thereof or a pharmaceutically acceptable salt of said aldose reductase inhibitor or said prodrug and of a selective serotonin reuptake inhibitor, a prodrug thereof or a pharmaceutically acceptable salt of said selective serotonin reuptake inhibitor or said prodrug. The amount of each of those ingredients may independently be, for example, 0.0001%–95% of the total amount of the composition, where the total amount may not, of course, exceed 100%. In any event, the composition or formulation to be administered will contain a quantity of each of the components of the composition according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: an aldose reductase inhibitor, a prodrug thereof or a salt of such aldose reductase inhibitor or said prodrug; and a selective serotonin reuptake inhibitor, a prodrug thereof or a salt of said selective serotonin reuptake inhibitor or said prodrug as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of the aldose reductase inhibitor can consist of one tablet or capsule while a daily dose of the SSRI can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compositions of this invention generally will be administered in a convenient formulation.

What is claimed is:

1. A pharmaceutical composition comprising an aldose reductase inhibitor (ARI), a prodrug thereof or a pharmaceutically acceptable salt of said ARI or said prodrug; a selective serotonin reuptake inhibitor, a prodrug thereof or a pharmaceutically acceptable salt of said selective serotonin reuptake inhibitor or said prodrug; and a pharmaceutically acceptable carrier, vehicle or diluent.

2. A composition of claim 1 wherein said ARI is fidarestat, epalrestat, minalrestat, SPR-210, zenarestat or zopolrestat, a prodrug thereof or a pharmaceutically acceptable salt of said ARI or of said prodrug.

3. A composition of claim 2 wherein said ARI is zopolrestat, a prodrug thereof or a pharmaceutically acceptable salt of zopolrestat or of said prodrug.

4. A composition of claim 1 wherein said selective serotonin reuptake inhibitor is femoxetine, fluoxetine, fluvoxamine, indalpine, indeloxazine, milnacipran, paroxetine, sertraline, sibutramine or zimeldine, a prodrug thereof or a pharmaceutically acceptable salt of said selective serotonin reuptake inhibitor or of said prodrug.

5. A composition of claim 4 wherein said selective serotonin reuptake inhibitor is sertraline or fluoxetine.

6. A composition of claim 5 wherein said ARI is fidarestat, epalrestat, minalrestat, SPR-210, zenarestat or zopolrestat, a prodrug thereof or a pharmaceutically acceptable salt of said ARI or of said prodrug.

7. A composition of claim 6 wherein said ARI is zopolrestat, a prodrug thereof or a pharmaceutically acceptable salt of zopolrestat or of said prodrug.

8. A method of treating a diabetic complication in a mammal comprising administering to said mammal a pharmaceutical composition of claim 1.

9. A method of claim 8 wherein said selective serotonin reuptake inhibitor is femoxetine, fluoxetine, fluvoxamine, indalpine, indeloxazine, milnacipran, paroxetine, sertraline, sibutramine or zimeldine, a prodrug thereof or a pharmaceutically acceptable salt of said selective serotonin reuptake inhibitor or of said prodrug.

10. A method of claim 9 wherein said ARI is fidarestat, epalrestat, minalrestat, SPR-210, zenarestat or zopolrestat, a prodrug thereof or a pharmaceutically acceptable salt of said ARI or of said prodrug.

11. A method of claim 10 wherein said ARI is zopolrestat, a prodrug thereof or a pharmaceutically acceptable salt of zopolrestat or of said prodrug and said selective serotonin reuptake inhibitor is sertraline or fluoxetine, a prodrug thereof or a pharmaceutically acceptable salt of said selective serotonin reuptake inhibitor or said prodrug.

12. A method of claim 11 wherein said diabetic complication is diabetic neuropathy.

13. A method of claim 11 wherein said diabetic complication is diabetic nephropathy.

14. A method of claim 11 wherein said diabetic complication is diabetic cardiomyopathy.

15. A method of claim 11 wherein said diabetic complication is diabetic retinopathy.

16. A method of claim 11 wherein said diabetic complication is cataracts.

17. A method of claim 11 wherein said diabetic complication is myocardial infarction.

18. A method of treating a diabetic complication in a mammal comprising administering to said mammal an ARI, a prodrug thereof or a pharmaceutically acceptable salt of said ARI or of said prodrug and a selective serotonin reuptake inhibitor, a prodrug thereof or a pharmaceutically acceptable salt of said selective serotonin reuptake inhibitor or of said prodrug.

19. A method of claim 18 wherein said selective serotonin reuptake inhibitor is femoxetine, fluoxetine, fluvoxamine, indalpine, indeloxazine, milnacipran, paroxetine, sertraline, sibutramine or zimeldine, a prodrug thereof or a pharmaceutically acceptable salt of said selective serotonin reuptake inhibitor or of said prodrug.

20. A method of claim 19 wherein said ARI is fidarestat, epalrestat, minalrestat, SPR-210, zenarestat or zopolrestat, a prodrug thereof or a pharmaceutically acceptable salt of said ARI or of said prodrug.

21. A method of claim 20 wherein said ARI is zopoirestat, a prodrug thereof or a pharmaceutically acceptable salt of zopolrestat or of said prodrug and said selective serotonin reuptake inhibitor is sertraline or fluoxetine, a prodrug thereof or a pharmaceutically acceptable salt of said selective serotonin reuptake inhibitor or said prodrug.

22. A method of claim 18 wherein the ARI, prodrug thereof or pharmaceutically acceptable salt of said ARI or said prodrug and the selective serotonin reuptake inhibitor, prodrug thereof or pharmaceutically acceptable salt of said selective serotonin reuptake inhibitor are administered separately.

23. A method of claim 18 wherein the ARI, prodrug thereof or pharmaceutically acceptable salt of said ARI or said prodrug and the selective serotonin reuptake inhibitor, prodrug thereof or pharmaceutically acceptable salt of said selective serotonin reuptake inhibitor are administered together.

24. A kit comprising:
a) a first unit dosage form comprising an aldose reductase inhibitor (ARI), a prodrug thereof or a pharmaceutically acceptable salt of said ARI or said prodrug and a pharmaceutically acceptable carrier, vehicle or diluent;
b) a second unit dosage form comprising a selective serotonin reuptake inhibitor, a prodrug thereof or a pharmaceutically acceptable salt of said selective serotonin reuptake inhibitor or said prodrug and a pharmaceutically acceptable carrier, vehicle or diluent; and
c) a container.

25. A kit of claim 24 wherein said selective serotonin reuptake inhibitor is femoxetine, fluoxetine, fluvoxamine, indalpine, indeloxazine, milnacipran, paroxetine, sertraline, sibutramine or zimeldine, a prodrug thereof or a pharmaceutically acceptable salt of said selective serotonin reuptake inhibitor or of said prodrug.

26. A kit of claim 25 wherein said ARI is fidarestat, epalrestat, minalrestat, SPR-210, zenarestat or zopolrestat, a prodrug thereof or a pharmaceutically acceptable salt of said ARI or of said prodrug.

27. A kit of claim 26 wherein said ARI is zopolrestat, a prodrug thereof or a pharmaceutically acceptable salt of zopolrestat or of said prodrug and said selective serotonin reuptake inhibitor is sertraline or fluoxetine, a prodrug thereof or a pharmaceutically acceptable salt of said selective serotonin reuptake inhibitor or said prodrug.

* * * * *